United States Patent [19]

Yasue et al.

[11] Patent Number: 5,834,269
[45] Date of Patent: Nov. 10, 1998

[54] METHOD OF INTRODUCING EXOGENOUS GENES INTO CULTURED CELLS OR FERTILIZED EGGS

[75] Inventors: Hiroshi Yasue, Ibaraki-ken; Hiraku Shimada; Koji Akasaka, both of Hiroshima-ken, all of Japan

[73] Assignees: National Institute of Animal Industry, Ibaraki-ken; Hiroshima University, Higashihiroshima, both of Japan

[21] Appl. No.: 883,344

[22] Filed: Jun. 26, 1997

[30] Foreign Application Priority Data

Jan. 17, 1997 [JP] Japan ................. 9-006550

[51] Int. Cl.⁶ .................. C07H 21/04; C12N 15/00
[52] U.S. Cl. .................. 435/172.3; 536/24.1
[58] Field of Search ............. 435/172.3, 325; 536/24.1

[56] References Cited

U.S. PATENT DOCUMENTS 5,610,053  3/1997  Chung et al. ............ 435/172.3
5,650,298  7/1997  Bujard et al. ............ 435/69.7

OTHER PUBLICATIONS

Chung et al. (Aug. 1993) A 5' element of the chicken beta–globin domain serves as an insulator in human erythroid cells and protects against position effect in Drosophila. Cell 74:505–514.

*Primary Examiner*—George C. Elliott
*Assistant Examiner*—Robert Schwartzman
*Attorney, Agent, or Firm*—Nikaido, Marmelstein, Murray & Oram LLP

[57] ABSTRACT

There is provided a method of introducing exogenous genes into cultured cells or fertilized eggs, characterized in that each exogenous gene is introduced into chromosomal DNA in a cultured cell or fertilized egg under a condition where the exogenous gene is placed between insulators so as to ensure an insulated environment, such that the introduced exogenous gene will not be affected by any influence from adjacent genes in the cultured cell or fertilized egg.

8 Claims, 2 Drawing Sheets

# METHOD OF INTRODUCING EXOGENOUS GENES INTO CULTURED CELLS OR FERTILIZED EGGS

BACKGROUND OF THE INVENTION

The present invention relates to a gene introduction technique for use in various scientific researches and industries, such as biological research and industry, medical research and industry, livestock research and industry, and fishery research and industry. In particular, the present invention relates to a method of introducing exogenous genes into cultured cells or fertilized eggs.

Recently, with the development of exogenous gene introduction technique, it has become possible to produce new biological varieties having new and useful forms/properties, thereby providing transgenic organisms. This is considered to be an extremely significant achievement which have never been reached before.

Up till now, there have been various methods which are used as exogenous gene introduction technique to introduce genes (cloned on plasmid vectors) into cultured exogenous cells or fertilized eggs. Such methods include, for example, calcium phosphate method, microinjection method, virus vector-method, and particle gun method.

The above methods such as particle gun method is known to be one of the most useful methods for introducing exogenous genes into cultured cells or fertilized eggs. In the past, the particle gun method was mainly used to introduce exogenous genes into plant cells (having cell walls) to greatly increase the plant varieties. However, in recent years, it has been suggested that the particle gun method should also be used to introduce exogenous genes into animal eggs to increase the animal varieties.

In fact, the particle gun method may be used to introduce exogenous genes into sea urchin eggs, or to introduce exogenous genes into eggs of some other invertebrates. Further, with some improvements, the particle gun method can be used to introduce exogenous genes into fish eggs covered with relatively hard shells, making it possible to simultaneously treat a large amount of fish eggs so as to purposefully and effectively produce new varieties of fishery products.

When the particle gun method is used to introduce exogenous gene into animal eggs, gold or tungsten particles coated with gene (DNA) substance are accelerated by virtue of a pressurized gas so as to be injected into cultured cells or fertilized eggs. After introduction of exogenous genes into animal eggs in this way, the genes introduced in the eggs may be found on prism embryos, whilst the metal particles can be removed from embryos at a late step.

However, when any one of the above prior art methods is used to introduce exogenous genes into cultured cells or fertilized eggs, there is a common problem that it is impossible to control introduction positions on chromosome DNA into which exogenous genes are to be introduced. As a result, the introduced exogenous genes are exposed to an environment under influence from adjacent genes in the cultured cell or fertilized eggs.

As indicated in FIG. 2, when an exogenous gene is introduced into a position close to inactive chromatin DNA, the introduced exogenous gene will become inactive due to the influence from the inactive chromatin DNA. As a result, there will be only extremely low efficiency in the production of transgenic organism. On the other hand, when an exogenous gene is introduced into a position close to active chromatin DNA, the introduced exogenous gene will become active due to the influence from the active chromatin DNA. This is because the introduced gene will be affected by strong enhancers in the active chromatin DNA, resulting in some problems such as excessive expression of the introduced genes, expression of the introduced genes which have become period-singular or organization-singular, making it impossible to produce desired transgenic organism.

SUMMARY OF THE INVENTION

It is an object of the present invention to provide an improved exogenous gene introduction method permitting correct expression of introduced exogenous gene so as to produce desired transgenic organism, thereby solving the above-mentioned problems peculiar to the above-mentioned prior arts.

According to the present invention, there is provided a method of introducing exogenous genes into cultured cells or fertilized eggs, characterized in that each exogenous gene is introduced into chromosome DNA in a cultured cell or fertilized egg under a condition where the exogenous gene is placed between insulators so as to ensure an insulated environment, such that the introduced exogenous gene will not be affected by any influence from adjacent genes in the cultured cell or fertilized egg.

Domain boundaries or insulator elements have been defined by two characteristic effects on gene expression; they confer position-independent transcription to transgenes stably integrated in the chromosome and they buffer a promoter from activation by enhancers when located between the two. David a. Gdula, et al. Proc. Natl. Acad. Sci. USA 93, 9378–9383, 1996 Title: Genetic and molecular analysis of the gypsy chromatin insulator of Drosophila.

According to one aspect of the present invention, the insulators are insulator fragments which before use exist in an upstream region of urchin arylsulfatase gene. In detail, the insulators are insulator fragments which before use exist in a range of about -2686bp -2115bp in an upstream region of urchin arylsulfatase gene.

According to another aspect of the present invention, the insulator fragments are combined with plasmids of exogenous genes, such that each exogenous gene to be introduced into a cultured cell or fertilized egg is placed between insulator fragments.

According to a further aspect of the present invention, the insulator fragments are capable of completely shutting off the activity of enhancers of an arylsulfatase gene upon being inserted between enhancers and promoters of the arylsulfatase gene.

The above objects and features of the present invention will become more understood from the following description with reference to the accompanying drawings.

DETAILED DESCRIPTION OF THE PREFERRED EMBODIMENTS

Figure 1:
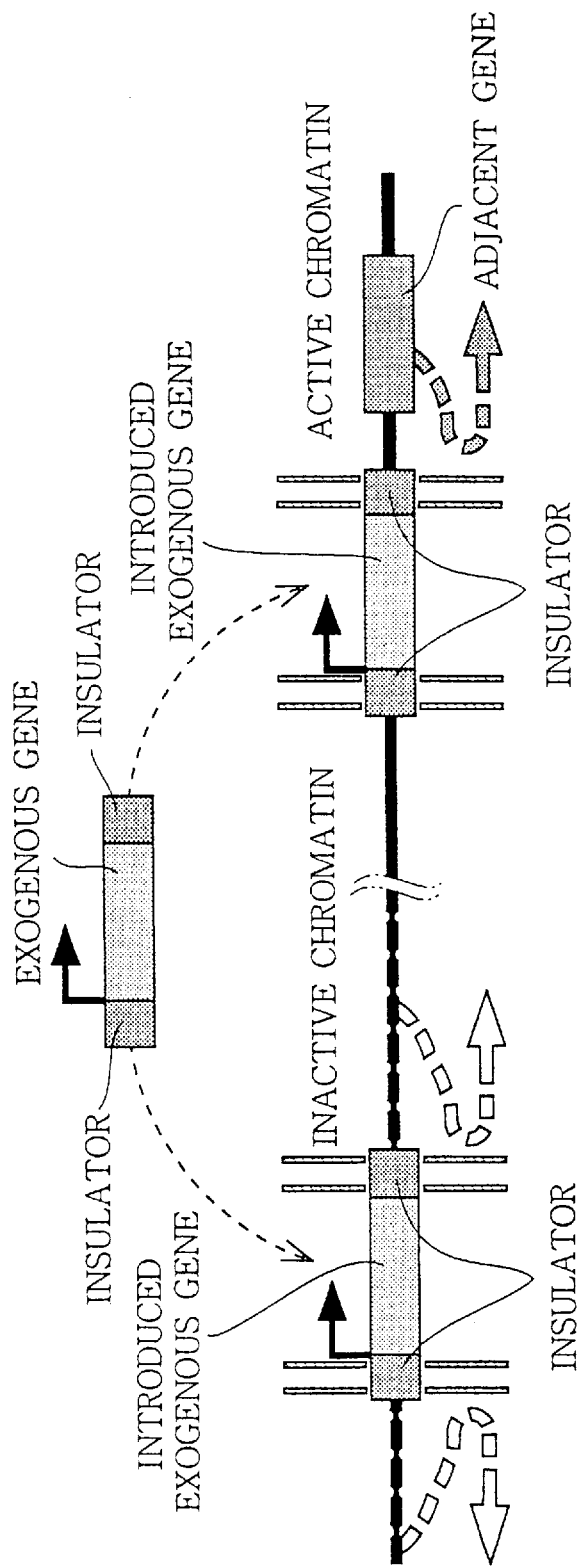
FIG. 1 is a schematic explanatory view indicating the mechanism of a method according to the present invention.
Figure 2:
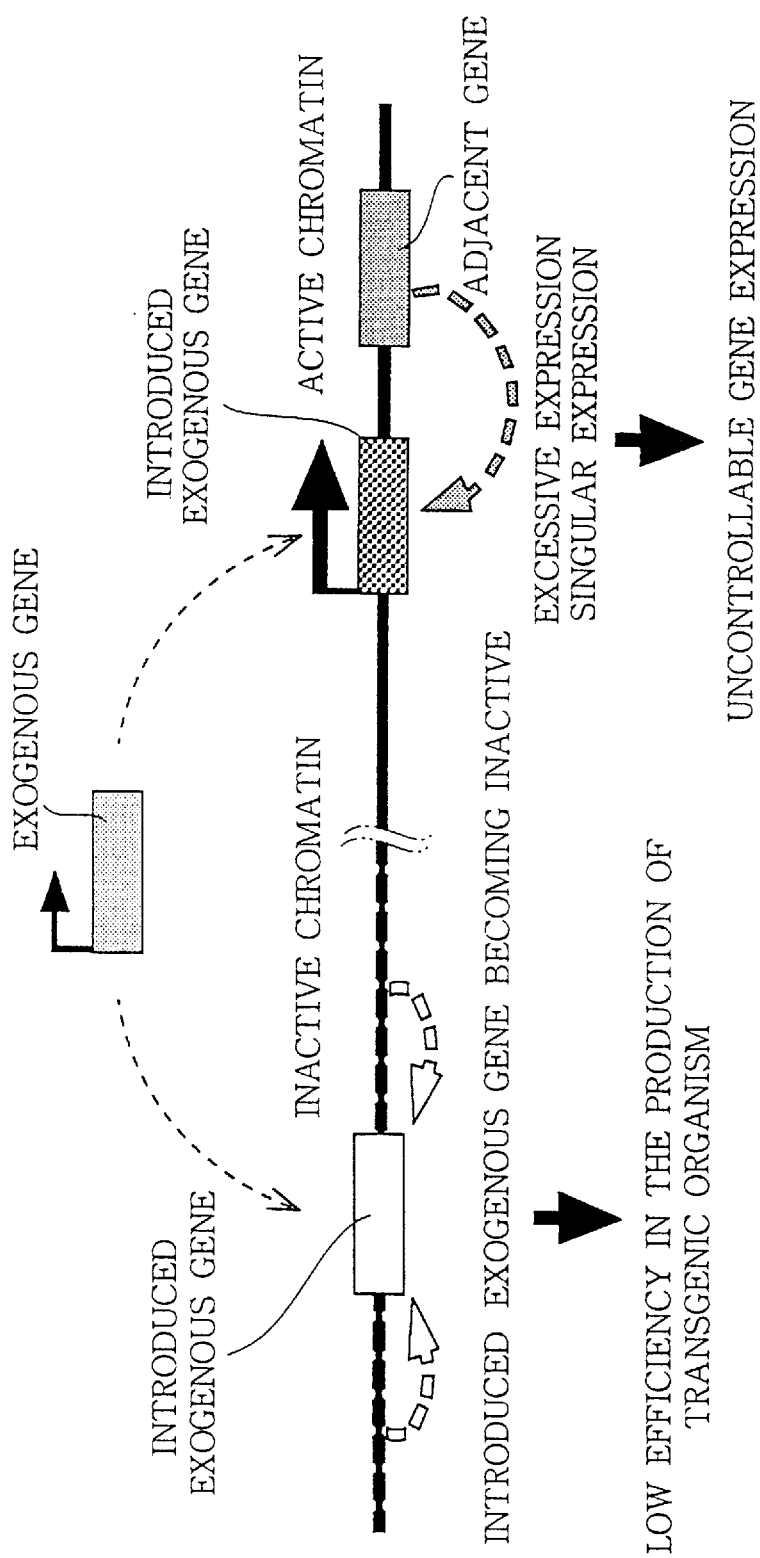
FIG. 2 is a schematic explanatory view indicating the mechanism of a method according to prior art.

Referring to FIG. 1, in a method according to the present invention, an exogenous gene is introduced into chromosome DNA in a cultured cell or fertilized egg under a condition where the exogenous gene is placed between insulators so as to ensure an insulated environment, such that the introduced exogenous gene will not be affected by any influence from adjacent genes in the cultured cell or fertilized egg.

It is understood from FIG. 1 that when an exogenous gene is introduced into a position close to inactive chromatin DNA, the introduced exogenous gene, owing to the effects of insulators positioned on both sides thereof, will not become inactive since the influence from the inactive chromatin DNA will be shutoff by the insulators. On the other hand, when an exogenous gene is introduced into a position close to active chromatin DNA, the introduced exogenous gene, also owing to the effects of insulators positioned on both sides thereof, will not become too active since the insulators are able to shut off the effect of strong enhancers in the active chromatin DNA, thereby avoiding some problems such as excessive expression of the introduced exogenous gene, or expression of an introduced exogenous gene which has become period-singular or organization-singular.

In this way, since it is possible to shut off the influence from adjacent genes, each exogenous gene introduced into a cultured cell or fertilized egg will be sure to express normally and stably on the chromosome DNA thereof, irrespective of (without having to depend on) insertion position of the exogenous gene in the chromosome DNA, making it possible to produce desired transgenic organism with an improved higher efficiency.

The method of the present invention will be described in more detail below with reference to the following example.

The insulators used in the following example are insulator fragments which before use exist in a range of 2686bp~2115bp in an upstream region of urchin arylsulfatase gene.

The insulator fragments are combined with plasmids of exogenous genes, such that each exogenous gene to be introduced into a cultured cell or fertilized egg is placed between insulator fragments. In this way, the introduced exogenous gene will not be affected by any influence from adjacent genes in the cultured cell or fertilized egg.

Attempts to define the nature of regulatory sequences present in eukaryotic genes by examining their expression after stable transformation into cultured cells or integration into the germ line of transgenic animals have concluded that the expression of the transgene is determined by its site of insertion within the genome. In some cases, the variegated pattern of expression of the transgene is reminiscent of effects on transcription caused by the proximity of heterochromatic sequences. This finding suggests that the chromatin structure of sequences adjacent to the insertion site determines the level of activation of the transgene, and that the eukaryotic genome contains regions of "condensed" chromatin unfavorable to gene expression and regions of "open" chromatin permissive to transcription. These higher order domains of chromatin structure were postulated to be defined by boundary elements, DNA sequences with a peculiar chromatin structure that separate regions with different degrees of permissiveness to gene expression. These boundary or insulator elements could then inhibit cross-regulatory interactions between transcription signals located in adjacent domains. A consequence of this property is that insulators should be able to inhibit the interaction of an enhancer with a promoter when located between the two without affecting the integrity of the enhancer.

To demonstrate the ability of the putative insulator fragment to inhibit the interference (position effect which represses the transcriptional activity) from the adjacent chromatin, the neo-reporter gene which is flanked by either putative insulator fragment or control DNA fragment is stable transfected into culture cells and the number of neo-resistant cells are determined. The number of neo-resistant cells increases when the neo-reporter gene is flanked by the insulator. Jay H. Chung, et al. Cell 74,505–514,1993 Title: A 5' element of the chicken β-globin domain serves as an insulator in human erythroid cells and protects against position effect in Drosophila.

For the enhancer-blocking assay, well-characterized enhancer and promoter should be chosen. For example, the Drosophila yp-1 enhancer is responsible for directing the appropriate stage-, sex-, and tissue-specific expression of the yolk protein genes. The putative insulator fragment (referred to as scs) derived from the proximal side of the 87 A7 heat shock locus of Drosophila is placed between the yp-1 enhancer and the hsp70 promoter. Several independent transgenic lines are generated from this construct. The transgenic animals are then dissected and stained for β-galactosidase activity. The enhancer-blocking by the scs insulator is confirmed. Rebecca Kellum & Paul Schedl, Mol. Cell. Biol. 12,2424–2431,1992 Title: A group of scs elements function as domain boundaries in an enhancer-blocking assay.

During actual operation for introducing genes into cultured cells or fertilized eggs, exogenous genes (DNA) and the insulator fragments are all linearized with a restriction enzyme, so that they may all possess the same restriction enzyme ends. By mixing the exogenous genes (DNA) with insulator fragments and then introducing the exogenous genes thus treated into cultured cells or fertilized eggs, the insulator fragments can sufficiently provide the above-mentioned insulating effect.

Seven DNA fragments have been reported as insulators up until now. The length of these DNA fragments is quite different, the shortest one is 340 bases and the longest one extends to a few kilo bases. There is no similarity between all the reported insulator sequences.

The sequence characteristics of sea urchin arylsulfatase are as follows:

CCCGGGAGCAGAACCCCTGTAAGCT-CAGGGGTTTTTAGGCGTTTMT TACGGTCAGAT-GAGCAATTTTTGATACCTTMATTTGT-TGTGACACTGGT AGTTMCTATTCATTCTTTCTTGCTCTCT-TGCTTTCTATTTCTCTTTA A ATGCTTTTCCAAAA-GAATGGGGGGGGGGGGCTGGACGCTCCCGAA C CCCGACGTTCCGCGGGCCCTGACATGT-MGCATCTCAAGAAGCATAT TTCTTGCCTGGCTGTT-MITTTACAAACGCATAAAAAAAATATATTTACT AAAGAATGAGGAAAAATCTCGGGAAGT-TATGTMTTTCAGCATTATG T GTAAACCACCGT-TATGGMTMGAAATAAACCACATTTCAATTTATTTC CCCCGAGCCCCCCTCCCCGAT-CAATACGCCAGTGCCCCGCCCCGCC CGCCTC-CCGATCTACACTTTGTTGGCG-GAAAAAATCGCAACTGATCTC CCCTACCTTTCTTCTTTCTCTTTCCCT-TGCTCTCCTCTTACCCTTTCCCT TCCCCACCCT-TCTCCACMCTTGTTGGCGGGATTACCTG-CAAATTATC TATT (SEQ ID NO:1)

Drosophila Gypsy Insulators are as follows:

MTTTATTCGCAAAAACATTG-CATATTTTCGGCAAAGTAMATTTTGT T GCATACCT-TATCAAAAATAAGTGCTGCATACTTTT-

TAGAGAAACCAAA
TAATTTTTATTGCATACCCGTTTT-
TAATAAAATACATTGCATACCCTCT TTT-
MTAAAAATATTGCATACTTTGACGAAA-
CAAATTTTCGTTGCATAC
CCMTAAAAGATTATTATATTGCATACCCGI T1
TAAAATACATTGC ATACCCTC I I iAATAAAAAATAT-
TGCATACGTTGACGAAACAAATTTTC GTTGCATAC-
CCAATAAMGATTATTATATTGCATAC-
CTTTTCTTGCCAT A (SEQ ID NO:2)

EXAMPLE

Preparation of Fertilized Eggs

A certain amount of sea urchin eggs obtained from Japanese sea were fertilized in seawater. Then, the fertilized urchin eggs were washed twice using the same seawater. Afterwards, approximately 0.15 ml of the fertilized eggs were placed on a filter paper moistened with seawater. In this way, the fertilized eggs were caught up with fibers of the filter paper so as to be fixed on the filter paper.

Preparation of DNA-coated Gold Particles

Gene (DNA) to be introduced into fertilized eggs were linearized with the use of a restriction enzyme to obtain restriction enzyme ends. Then, the gene (DNA) thus treated were mixed with urchin chromosome DNA (completely digested with the use of the same restriction enzyme and having an amount which was 8 times the above treated gene), and also mixed with insulator fragments which had been linearized to obtain the same restriction enzyme ends, thus producing a DNA solution having DNA concentrate of 0.5 mg/ml.

The gold particles (1 µm in diameter) were coated with the linearized plasmid containing fusion gene (3 µg DNA/ mg particle) by coprecipitation in 7.5% polyethylene glycol 6000, 0.94 M NaCl. After washing with ethanol, the ethanol suspension of the DNA-coated gold particles was placed on the surface of the projectile, after which it was dried and used for bombardment.

Afterwards, 2.5 mg of dry gold particles (having a diameter of 1 µand have been sonicated in 100% ethanol solution) were suspended in 20 µl of the above DNA solution. Further added into the above DNA solution was 12 µ 1 of autoclave-disinfected PEG solution (which may be obtained by dissolving polyethylene glycol in 2.5M NaCl so that the solution has a PEG concentration of 20% by weight), followed by ice-cooling for 20 minutes. In this process, the DNA were deposited on the surfaces of gold particles. Subsequently, the upper layer of the DNA solution is removed by virtue of centrifugal separation, thus obtaining DNA-coated gold particles. Finally, the DNA-coated gold particles are subjected to a further treatment by being suspended in 62.5 µl of 100% ethanol in a mixer.

Introduction of Gene (DNA) into Fertilized Eggs 0.8 mg of DNA-coated gold particles were placed on the surface of a polyethylene projectile and were set in a particle gun, so that the DNA-coated gold particles could be emitted outwardly with an initial speed of 350 m/s under a pressure of 0.1 atmosphere, thereby obtaining an energy for DNA-coated gold particles to bombard into the fertilized eggs fixed on the above filter paper.

The pneumatic particle acceleration device has a barrel to which an air chamber is connected at the bottom end. The air chamber is equipped with a plunger pump at one side and an exhaust valve at the other. The maximum pressure of the device was more than 220 kg/cm$^2$, at which the initial velocity of the projectile was 330 m/s as determined by an electronic velocity meter. A metal stopper designed to stop the plastic projectile is connected at the top end of the barrel. The barrel is fixed vertically in a plastic vacuum desiccator that is placed in a laminar flow hood.

100,000 fertilized eggs were placed on a filter paper on funnel with glass. The funnel with the eggs was turned upside down and placed 10 cm over the stopper.

A polyethylene projectile with the top surface covered with DNA-coated gold particles was introduced from the top and placed at the bottom end of the barrel. Air was compressed with a plunger and accumulated in the chamber. After the pressure in the desiccator had been reduced to 110 mm Hg, the compressed air was released instantaneously from the chamber to the barrel by triggering the exhaust valve. The projectile accelerated in the barrel and collided with the stopper, "stabbing" into it and sealing off the aperture. The gold particles continued on to the target eggs through an aperture in the stopper. After being bombarded, the eggs were removed from the filter paper by flushing with seawater and then cultured in dishes of filtered seawater. (Koji Akasaka et al. Mol. Marine Biol. Biotech. 4;255–261, 1955 Title: Introduction of DNA into sea urchin eggs by particle gun) (lida et al. Theor. Appl. Genet. 80, 813–816, 1990 Title: Gene delivery into cultured plant cells by DNA-coated gold particles accelerated by a pneumatic particle gun).

Evaluation on Normal Expressibility of Exogenous Genes Introduced in Fertilized Eggs Reporter genes such as CAT (chloramphenicol acetyltransferase) and Luc (luciferase) were utilized to perform evaluation on normal expressibility of exogenous genes introduced in fertilized eggs, and it was possible to confirm that with the use of insulator fragments in a manner as described above, the introduced exogenous genes will not be affected by any influence from adjacent genes in the cultured cells or fertilized eggs.

Here, the CAT and Luc were used as experimental genes which were respectively combined at downstream sides of promoters of histone H1 gene and arylsulfatase gene of urchin. By measuring the activities of products which are genes fused together, it was possible to confirm whether the introduced exogenous genes have expressed normally (in a desired manner) or not.

In detail, Luc was combined at the downstream side of promoter area of arylsulfatase gene to obtain a product (Ars 100-Luc), CAT was combined at the downstream side of promoter area of histone H1 gene to obtain a product (H1-CAT). Then, (Ars 100-Luc) and (H1-CAT) were linearized with the use of the same restriction enzyme, and were introduced into fertilized eggs. In this way, the introduced (Ars 100-Luc) and (H1-CAT) were fused together and combined with the exogenous genes previously introduced in fertilized eggs. As a result, it was found that arylsulfatase gene had expressed 6 times as much as its normal expression, thereby confirming that the previously introduced exogenous genes had expressed abnormally.

When the Ars 100-Luc construct was ligated with the insulator fragments on its both ends, the abnormal expression was not observed in the same experimental conditions described above, thereby confirming that the introduced exogenous genes had expressed normally (in a desired manner) with the use of insulator fragments.

It is understood from the above description that, with the use of the method according to the present invention, when exogenous genes are introduced into the cultured cells or fertilized eggs, it is possible to shut off the influence from adjacent genes, so that exogenous genes introduced into the cultured cells or fertilized eggs are sure to express normally (in a desired manner) and stably on chromosome DNA thereof, irrespective of (without having to depend on) insertion position of the exogenous gene in the chromosome DNA, making it possible to produce desired transgenic organism with an improved higher efficiency.

While the presently preferred embodiments of the this invention have been shown and described above, it is to be understood that these disclosures are for the purpose of illustration and that various changes and modifications may be made without departing from the scope of the invention as set forth in the appended claims.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
       ( A ) LENGTH: 582 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| CCCGGGAGCA | GAACCCCTGT | AAGCTCAGGG | GTTTTTAGGC | GTTTAATTAC | GGTCAGATGA | 60 |
| GCAATTTTTG | ATACCTTAAT | TTGTTGTGAC | ACTGGTAGTT | AACTATTCAT | TCTTTCTTGC | 120 |
| TCTCTTGCTT | TCTATTTCTC | TTTAAAATGC | TTTTCCAAAA | GAATGGGGGG | GGGGGGCTGG | 180 |
| ACGCTCCCGA | ACCCCGACGT | TCCGCGGGCC | CTGACATGTA | AGCATCTCAA | GAAGCATATT | 240 |
| TCTTGCCTGG | CTGTTAATTT | ACAAACGCAT | AAAAAAAATA | TAATTTACTA | AAGAATGAGG | 300 |
| AAAAATCTCG | GGAAGTTATG | TAATTTCAGC | ATTATGTGTA | AACCACCGTT | ATGGAATAAG | 360 |
| AAATAAACCA | CATTTCAATT | TATTTCCCCC | GAGCCCCCT | CCCGATCAA | TACGCCAGTG | 420 |
| CCCCGCCCCG | CCCGCCTCCC | GATCTACACT | TTGTTGGCGG | AAAAAATCGC | AACTGATCTC | 480 |
| CCCTACCTTT | CTTCTTTCTC | TTTCCCTTGC | TCTCCTCTTA | CCCTTTCCCT | TCCCCACCCT | 540 |
| TCTCCACAAC | TTGTTGGCGG | GATTACCTGC | AAATTATCTA | TT | | 582 |

( 2 ) INFORMATION FOR SEQ ID NO:2:

( i ) SEQUENCE CHARACTERISTICS:
       ( A ) LENGTH: 348 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:2:

| | | | | | | |
|---|---|---|---|---|---|---|
| AATTTATTCG | CAAAAACATT | GCATATTTTC | GGCAAAGTAA | AATTTTGTTG | CATACCTTAT | 60 |
| CAAAAAATAA | GTGCTGCATA | CTTTTAGAG | AAACCAAATA | ATTTTTTATT | GCATACCCGT | 120 |
| TTTAATAAA | ATACATTGCA | TACCCTCTTT | TAATAAAAAA | TATTGCATAC | TTTGACGAAA | 180 |
| CAAATTTTCG | TTGCATACCC | AATAAAGAT | TATTATATTG | CATACCCGTT | TTTAATAAAA | 240 |
| TACATTGCAT | ACCCTCTTTT | AATAAAAAAT | ATTGCATACG | TTGACGAAAC | AAATTTTCGT | 300 |
| TGCATACCCA | ATAAAGATT | ATTATATTGC | ATACCTTTTC | TTGCCATA | | 348 |

What is claimed is:

1. A method for introducing an exogenous gene into cultured cells or fertilized eggs so as to inhibit the effect of adjacent endogenous genes on transcription of the exogenous gene, comprising introducing into said cultured cells or fertilized eggs a nucleic acid comprising an exogenous gene, and located at each end of said gene, a nucleic acid fragment found in an upstream region of urchin arylsulfatase gene which functions as an insulator, and expressing said nucleic acid such that transcription of the exogenous gene occurs and the insulators inhibit the effect of adjacent genes on said transcription.

2. A method according to claim 1, wherein at least one of said DNA fragments consists of the nucleotide sequence of SEQ ID NO: 1.

3. A method according to claim 1, wherein said DNA fragments located at each end of said exogenous gene consist of the nucleotide sequence of SEQ ID NO: 1.

4. A method according to claims wherein said nucleic acid further comprises plasmid DNA.

5. A method according to claim 1, wherein said introducing nucleic acid into fertilized eggs comprises the steps of preparing particles coated with said nucleic acid and emitting said particles from a particle gun.

6. An isolated nucleic acid fragment of urchin arylsulfatase gene that consists of the nucleotide sequence of SEQ ID NO:1.

7. A nucleic acid for introduction and expression in a fertilized egg or cultured cell, said nucleic acid comprising:

at least one fragment according to claim 6, linked to an exogenous gene, such that during expression of said nucleic acid in said fertilized egg or cultured cell, said at least one fragment inhibits the effect of an adjacent endogenous gene of said fertilized egg or cultured cell upon transcription of said exogenous nucleic acid.

8. A claim according to claim 7, wherein said nucleic acid is expressed in a fertilized egg.

* * * * *